(12) United States Patent
Suzuki et al.

(10) Patent No.: US 9,745,249 B2
(45) Date of Patent: Aug. 29, 2017

(54) METHOD FOR THE PREPARATION OF BETA-SUBSTITUTED GAMMA-AMINO CARBOXYLIC ACIDS

(71) Applicant: SIEGFRIED LTD., Zofingen (CH)

(72) Inventors: Yoshikazu Suzuki, Zurich (CH); Irène Lehmann, Zurich (CH); Hans Ulrich Bichsel, Hoerhausen (CH); Thomas Bader, Zurich (CH); Sirinporn Thamapipol, Bang Mueang Mai (TH)

(73) Assignee: SIEGFRIED LTD., Zofingen (CH)

( * ) Notice: Subject to any disclaimer, the term of this patent is extended or adjusted under 35 U.S.C. 154(b) by 0 days.

(21) Appl. No.: 15/314,616

(22) PCT Filed: Jun. 2, 2015

(86) PCT No.: PCT/EP2015/062218
§ 371 (c)(1),
(2) Date: Nov. 29, 2016

(87) PCT Pub. No.: WO2015/189068
PCT Pub. Date: Dec. 17, 2015

(65) Prior Publication Data
US 2017/0114003 A1    Apr. 27, 2017

(30) Foreign Application Priority Data

Jun. 12, 2014 (EP) .................... 14172162

(51) Int. Cl.
*C07C 227/04* (2006.01)
*C07C 201/12* (2006.01)
*C07C 227/34* (2006.01)

(52) U.S. Cl.
CPC .......... *C07C 227/04* (2013.01); *C07C 201/12* (2013.01); *C07C 227/34* (2013.01)

(58) Field of Classification Search
None
See application file for complete search history.

(56) References Cited

U.S. PATENT DOCUMENTS

| | | | |
|---|---|---|---|
| 5,637,767 | A | 6/1997 | Grote et al. |
| 2005/0043565 | A1 | 2/2005 | Przewosny et al. |
| 2010/0324139 | A1 | 12/2010 | Gaitonde et al. |

FOREIGN PATENT DOCUMENTS

| | | |
|---|---|---|
| AR | 064949 A1 | 5/2009 |
| WO | 2006/110783 A2 | 10/2006 |
| WO | 2008/117305 A2 | 10/2008 |
| WO | 2009/081208 A1 | 7/2009 |
| WO | 2009/141362 A2 | 11/2009 |
| WO | 2009/147434 A1 | 12/2009 |
| WO | 2010/004577 A1 | 1/2010 |
| WO | 2011/016052 A2 | 2/2011 |
| WO | 2013/076225 A1 | 5/2013 |

OTHER PUBLICATIONS

Gopalan et al. Proceedings of the Indian Academy of Sciences—Section A, 1968, pp. 92-98.*
Sep. 1, 2015 International Search Report issued in International Patent Application No. PCT/EP2015/062218.
Dec. 15, 2016 International Preliminary Report on Patentability issued in International Patent Application No. PCT/EP2015/062218.
Mar. 20, 2015 Extended Search Report issued in European Patent Application No. 14172162.1.
Andruszkiewicz, Ryszard et al; "A Convenient Synthesis of 3-Alkyl-4-aminobutanoic Acids;" Communications; Dec. 1989; pp. 953-955.

* cited by examiner

*Primary Examiner* — Clinton Brooks
(74) *Attorney, Agent, or Firm* — Oliff PLC

(57) ABSTRACT

The present invention relates to the preparation of β-substituted γ-amino carboxylic acids, preferably in enantiomerically enriched or even enantiomerically pure form, by a one-pot conversion of a β-substituted γ-nitro dicarboxylic acid ester or of a β-substituted γ-nitro dicarboxylate of general formula to a β-substituted γ-nitro carboxylic acid and a subsequent reduction of the γ-nitro group to an amine group. In particular, the present invention relates to the preparation of (S)-pregabalin. In addition, the formation of enantiomerically enriched β-substituted γ-amino carboxylic acids and β-substituted γ-nitronate carboxylic acid salts are also described.

11 Claims, No Drawings

METHOD FOR THE PREPARATION OF BETA-SUBSTITUTED GAMMA-AMINO CARBOXYLIC ACIDS

The present invention relates to the preparation of β-substituted γ-amino carboxylic acids, preferably in enantiomerically enriched or even enantiomerically pure form. In particular, the present invention relates to the preparation of (S)-pregabalin.

The chemical name of (S)-pregabalin is (3S)-3-(aminomethyl)-5-methylhexanoic acid or (S)-(+)-4-amino-3-(2-methylpropyl)butanoic acid, and is also known as (S)-γ-amino β-isobutyl butyric acid or (S)-3-isobutyl GABA. It has the following chemical structure (S-IV*)

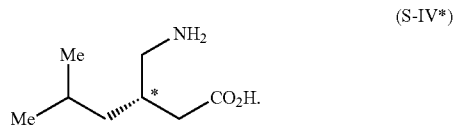 [SMILES: CC(C)C[C@H](CN)CC(=O)O]

(S)-Pregabalin is an anticonvulsant drug used for neuropathic pain and as an adjunct therapy for partial seizures with or without secondary generalization in adults. It has also been found effective for generalized anxiety disorder (GAD) and is (as of 2007) approved for this use in the European Union and Russia. (S)-Pregabalin is marketed by Pfizer under the trade name Lyrica. It is effective at treating some causes of chronic pain such as fibromyalgia but not others. It is considered to have a low potential for abuse, and a limited dependence liability if misused, but is classified as a Schedule V drug in the USA.

Racemic pregabalin was first reported in *Synthesis* (1989, S. 953). The synthetic process reported involved the addition of nitromethane to an ethyl 2-alkenoate and the nitro ester thus formed was reduced using palladium on carbon. Subsequent hydrolysis using hydrochloric acid afforded racemic pregabalin as the hydrochloride salt. The free base of racemic pregabalin was prepared by ion exchange chromatography.

An alternative process, reported in U.S. Pat. No. 5,637,767, utilizes the condensation of isovaleraldehyde with diethyl malonate. The 2-carboxy-2-alkenoic acid thus formed is then reacted with a cyanide source, specifically potassium cyanide, and the subsequent product is hydrolyzed using KOH to give the potassium salt of the cyano acid, which is hydrogenated in situ using sponge nickel and neutralized with acetic acid to give racemic pregabalin.

A further alternative method for the preparation of racemic pregabalin hydrochloride has been reported in US 2005/0043565. This process involves a Wittig-Horner reaction between isovaleraldehyde and triethyl phosphonoacetate to afford the ethyl 2-alkenoate. Addition of nitromethane followed by hydrogenation using Raney nickel affords the lactam, which is hydrolyzed using hydrochloric acid to form the hydrochloride salt of the amino acid. This route gives the hydrochloride salt instead of the free base and thus necessitates an additional transformation.

The above syntheses not only require long reaction times and/or many reaction steps and often afford the product in low yields or purities, but also have the following further disadvantages:
- Non-stereoselective synthesis, requiring additional steps and raw material for the resolution of the racemate, as well as the disposal of the undesired (and non-recyclable) enantiomer. Furthermore, recycling of the resolving agent may be laborious.
- Oily intermediates and thus difficult purification.
- Use of toxic reagents, such as KCN, requiring careful handling and disposal to avoid contamination.
- Use of a Wittig-Horner reaction, requiring additional steps for the preparation of the Wittig-Horner reagent and producing large amounts of waste.
- Formation of impure HCl salt of pregabalin, requiring additional purification steps and a transformation from the salt to the free base.

More recent methods also allow for the preparation of enantiomerically enriched or pure (S)-pregabalin:
- WO 2006/110783 discloses three different routes to (S)-pregabalin, involving (a) reduction of a nitro dicarboxylic ester (VI)

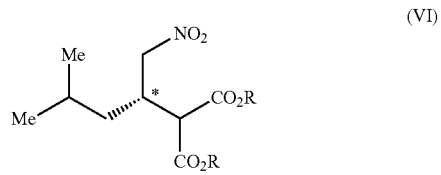

and subsequent hydrolysis/decarboxylation, (b) a decarboxylation of the nitro dicarboxylic ester (VI) and subsequent reduction/hydrolysis, and (c) reduction/lactamization of the nitro dicarboxylic ester (VI), followed by hydrolysis/decarboxylation and subsequent lactam opening, respectively.
- The methods of WO 2009/081208 and US 2010/0324139 both rely on the hydrolysis of ethyl 5-methyl-3-nitromethyl-hexanoate under basic conditions and subsequent hydrogenation.
- WO 2009/147434 describes a synthesis of (S)-pregabalin involving a one-pot hydrolysis/decarboxylation of the above nitro dicarboxylic ester (VI) under basic conditions, followed by reduction to the amine.
- According to WO 2011/016052, ethyl 5-methyl-3-nitromethyl-hexanoate is subjected to a one-pot hydrolysis/hydrogenation to afford racemic pregabalin, which may then be resolved with (S)-mandelic acid following the procedure of *Organic Process Research and Development* (1997, p. 26-38).
- Further alternatives, which involve the formation of a nitro isoxazole (VII)

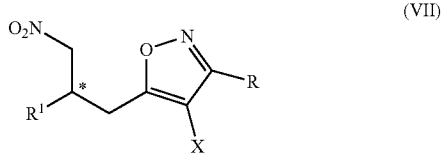

via a Michael addition of nitromethane, are described in WO 2013/076225. Said nitro isoxazole (VII) is hydrolyzed and reduced, or, alternatively, first reduced and then hydrolyzed to afford (S)-pregabalin.

All of the above methods have major drawbacks, such as low yields or purities, long reaction times and/or many reaction steps. Further disadvantages of these syntheses include the use of expensive reagents and/or catalysts, low atom economy and formation of significant amounts of waste (e.g. bromination of the alcohol using PPh₃ and BR₂ as described in WO 2009/081208); purification by column chromatography, which is not practicable on large scale; safety issues (e.g. use of NaH).

Also, some of the described reactions have been found to lack reproducibility:

In particular, WO 2009/147434 indicated a yield of 85-90% for the one-pot hydrolysis/decarboxylation of nitro dicarboxylic acid ester (VIII) to nitro acid (IX)

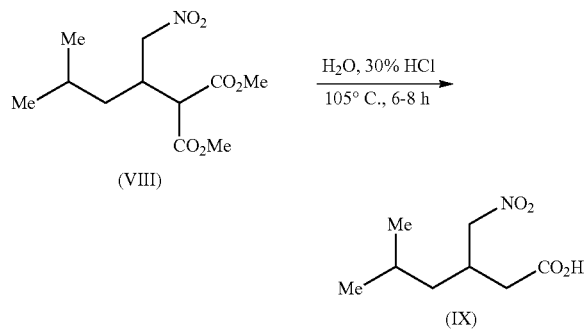

using 30% HCl (8.7 equiv.). However, upon reproduction, it was found that the reaction was not complete after 7 h (HPLC: 18% of product IX, 70% of intermediates, 10% of starting material VIII) and that there was also a by-product—dicarboxylic acid (X)—formed. After 14 hours, the reaction went to completion to afford a 46:54 mixture (determined by ¹H NMR spectroscopy) of (IX) and (X) in only 38% yield (determined by quantitative HPLC).

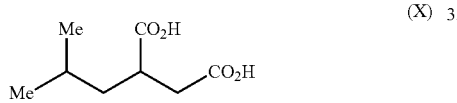

In WO 2011/016052, treatment of a slightly different nitro dicarboxylic acid ester (XI) with 47% HBr was reported to provide nitro acid (IX) as a solid after a reaction time of two days (yield not specified).

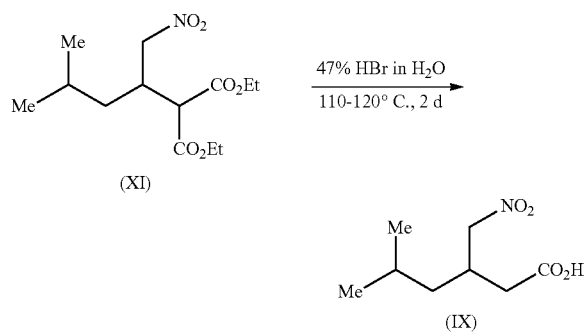

Unexpectedly, reproduction of the above conditions led to a completion of the reaction within 16 h, but instead of the desired product (which should be an oil), exclusively the dicarboxylic acid by-product (X) was obtained as a white solid.

WO 2006/110783 describes that a Krapcho reaction of nitro dicarboxylic acid ester (XI) can afford the corresponding nitro ester (XII) in 5 h (yield not specified).

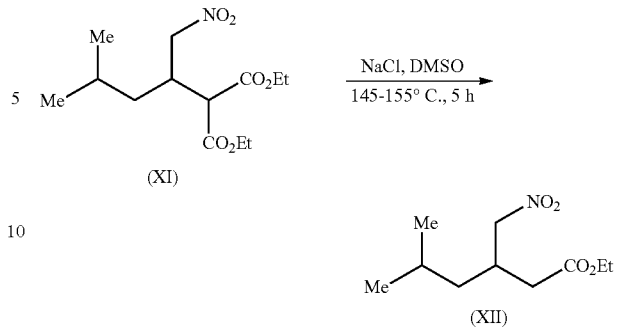

Applying the conditions described in WO 2006/110783 to the corresponding methyl ester (VIII), nitro acid (IX) was obtained in only 38% yield (determined by quantitative HPLC). The drawback of this reaction is, however, not just the low yield, but also that one additional reaction step (hydrolysis of the ester group) is necessary.

In a slightly different approach, WO 2008/117305 describes a one-pot hydrolysis/decarboxylation of a racemic Meldrum's acid derivative (XIII) by treatment with pTsOH in toluene to afford nitro carboxylic acid (IX) in 86% yield.

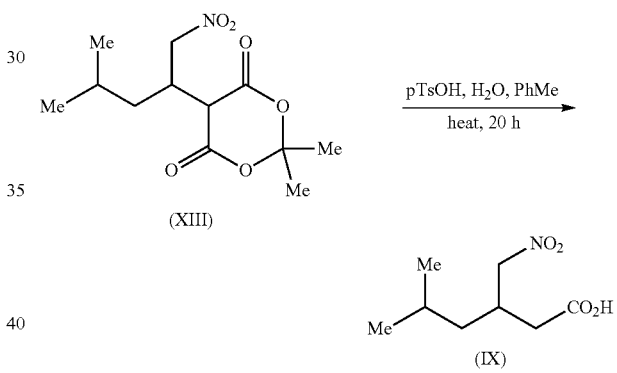

Attempted application of this reaction to the corresponding methyl ester (VIII) failed. Further disadvantages of this synthetic strategy are high costs for the Meldrum's acid derivative and the fact that his reaction is not stereoselective, such that the undesired enantiomer has to be removed and disposed of.

Therefore, the hydrolysis/decarboxylation of compounds of formula (VI) is very difficult due to significant side reaction at the nitro-alkyl group, resulting in loss of yield and/or contamination of the products. The above described problems when trying to reproduce the published procedures clearly confirm this fact.

For this reason, it is a problem of the present invention to provide an improved method for the preparation of β-substituted γ-amino carboxylic acids in general, and in particular of (S)-pregabalin.

This problem has been solved by the method according to claim 1. Preferred embodiments are subject of the dependent claims.

In a first aspect, the present invention refers to a method for the preparation of a β-substituted γ-amino carboxylic acid of general formula (I)

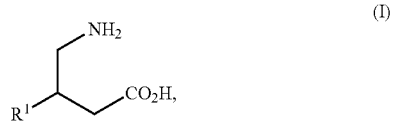

(I)

comprising a one-pot conversion of a β-substituted γ-nitro dicarboxylic acid ester or of a β-substituted γ-nitro dicarboxylate of general formula (II) to a β-substituted γ-nitro carboxylic acid of general formula (III)

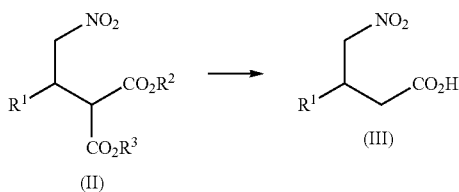

and a subsequent reduction of the γ-nitro group to an amine group.

The one-pot conversion of (II) to (III) involves the treatment of (II) with 0.2 to 10 equivalents of a strong Brønsted acid S using a carboxylic acid C as solvent in the presence of 1 to 15 equivalents of water at a temperature of between 90° C. and 120° C. and a concentration of less than 1 M.

The pKa of the strong acid Brønsted S is preferably <0.

The carboxylic acid C is an aliphatic carboxylic acid having a melding point of <25° C., and is preferably a C1- to C3-alkyl carboxylic acid, in particular AcOH.

Lower reaction temperatures generally increase the reaction time and may result in loss of yield due to incomplete conversion, while higher temperatures may result in decomposition of the product.

The reduction may be performed directly after the one-pot conversion of (II) to (III), or there may be a number of other steps between these two reactions. Many procedures for the reduction of a nitro group to an amine are well known in the field, and the person skilled in the art is able to select suitable conditions that will not affect the other functional groups present in the molecule based on his general technical knowledge. For instance, a metal catalyzed hydrogenation may be used in many cases.

In the above structures and throughout this application, $R^1$ is selected from the group consisting of $C_1$- to $C_{12}$-alkyl, alkenyl, alkynyl, and aryl, and $R^2$ and $R^3$ are independently from one another selected from the group consisting of a $C_1$- to $C_{12}$-alkyl or aryl group, an alkali metal ion or a tetra-substituted ammonium ion, or $R^2$ and $R^3$ are together forming a $C_3$- to $C_{12}$-alkyl, alkenyl or aryl ring structure or are an alkaline earth metal ion.

Throughout this application, the term "alkyl" refers to a monovalent saturated hydrocarbon group, which may be linear or branched or include a cyclic moiety. An alkyl group may be optionally substituted and/or include one or more heteroatoms, such as N, O or S, in its carbon skeleton. Preferably, an alkyl group is linear or branched. Preferably, an alkyl group is not substituted and does not include heteroatoms. Examples of alkyl groups are methyl, ethyl, propyl, iso-propyl, butyl, iso-butyl, sec-butyl, tert-butyl, pentyl, neo-pentyl, cyclopentyl, hexyl, cyclohexyl, heptyl and cycloheptyl. Preferably, an alkyl group is a $C_1$-$C_{12}$ alkyl group, more preferably a $C_1$-$C_6$ alkyl group.

Throughout this application, the term "alkenyl" refers to a monovalent hydrocarbon group, which comprises at least one carbon-carbon double bond. An alkenyl group may be linear or branched or include a cyclic moiety. An alkenyl group may be optionally substituted and/or include one or more heteroatoms, such as N, O or S, in its carbon skeleton. Preferably, an alkenyl group is linear or branched. Preferably, an alkenyl group is not substituted and does not include heteroatoms. Examples of alkenyl groups are vinyl, allyl, but-1-enyl, cyclohexenyl and cycloheptenyl. Preferably, an alkenyl group is a $C_2$-$C_{12}$ alkenyl group, more preferably a $C_2$-$C_6$ alkenyl group.

Throughout this application, the term "alkynyl" refers to a monovalent hydrocarbon group, which comprises at least one carbon-carbon triple bond. An alkynyl group may be linear or branched or include a cyclic moiety. An alkynyl group may be optionally substituted and/or include one or more heteroatoms, such as N, O or S, in its carbon skeleton. Preferably, an alkynyl group is linear or branched. Preferably, an alkynyl group is not substituted and does not include heteroatoms. Examples of alkynyl groups are ethynyl, propargyl, but-1-ynyl and but-2-ynyl.

Preferably, an alkynyl group is a $C_2$-$C_{12}$ alkynyl group, more preferably a $C_2$-$C_6$ alkynyl group.

Throughout this application, the term "aryl" refers to a monovalent aromatic hydrocarbon group. An aryl group may be optionally substituted and/or include one or more heteroatoms, such as N, O or S, in its carbon skeleton. Preferably, an aryl group is not substituted and does not include heteroatoms. Examples of aryl groups are phenyl, naphthyl and pyridyl. Preferably, an aryl group is a $C_4$-$C_{14}$ aryl group, optionally including heteroatoms, more preferably a $C_6$-$C_{10}$ aryl group.

An optionally substituted group may be substituted with one or more of F, Cl, Br, I, $CF_3$, OH, OR, SH, SR, $NH_2$, NHR, $NR_2$, $SiR_3$, CN, =O, or =S.

The method of the present invention allows for an efficient synthesis of β-substituted γ-nitro carboxylic acids of general formula (III) in high yield and few steps. Key feature of this method is the one-pot conversion of a β-substituted γ-nitro dicarboxylic acid ester or of a β-substituted γ-nitro dicarboxylate of general formula (II) to a β-substituted γ-nitro carboxylic acid of general formula (III), which involves a hydrolysis/decarboxylation.

The criticality of using nitroalkanes in synthesis is mainly due to their easy conversion into the corresponding nitronate anions under basic condition. Nitronate salts in turn can be simply hydrolyzed to carbonyl compounds (known as Nef reaction). In addition, primary nitroalkanes are not stable and can be converted to carboxylic acids and hydroxylamine in concentrated mineral acids at elevated temperature. These reactions have been described, e.g., by Edward et al. in *Can. J. Chem.* 1971, 49, 3483-3501 and by Eeden et al. in *J. Am. Chem. Soc.* 1993, 115, 9834-9835.

For γ-nitro acids, it has been found that treatment with refluxing AcOH/HCl for 2 hours will lead to the formation of the corresponding dicarboxylic acid (*Tetrahedron: Asymmetry*, 2008, p. 945). Also, it has been reported that phosphoryl 4-nitroalkanates are thermally unstable and undergo consecutive transformations while being heated.

Thus, as expected, simple treatment of a β-substituted γ-nitro dicarboxylic acid ester or of a β-substituted γ-nitro dicarboxylate of general formula (II) with a mineral acid at elevated temperature will lead to the formation of a number of by-products. For this reason, extensive optimization of the reaction conditions was necessary in order to arrive at the method of the present invention (see examples 1 and 2 below).

Thanks to the combination of a strong Brønsted acid S with a carboxylic acid C as the solvent in the presence of water, it has been possible to significantly reduce the amount of undesired by-products formed, in particular of dicarboxylic acid (XIII) and of N-hydroxy succinimide (XIV).

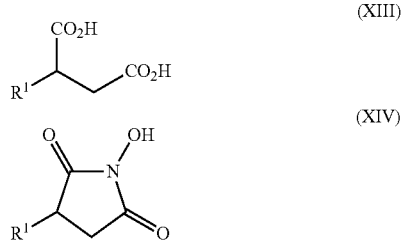

The exact reaction pathway of the one-pot hydrolysis and decarboxylation is hence still unknown. However, it is expected that this reaction proceeds via a number of different intermediates, ultimately leading to the formation of (III).

Methods for the preparation of β-substituted γ-nitro dicarboxylic acid esters (II) are generally known. For instance, dimethyl 2-(4-methyl-1-nitropentan-2-yl) malonate (XVI) may be prepared by an asymmetric Michael addition (e.g. using cupreidine) of dimethyl malonate to 4-methyl-1-nitropent-1-ene (XV):

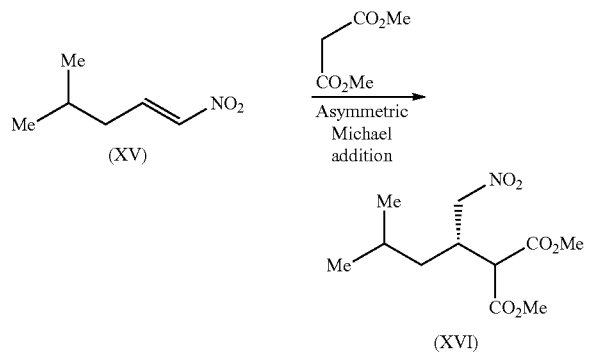

If desired, saponification will afford the corresponding dicarboxylate salt.

Also the conversion from the β-substituted γ-nitro carboxylic acid (III) to the β-substituted γ-amino carboxylic acid (I) is generally known. For instance, a hydrogenation may be used.

The one-pot conversion of (II) to (III) as described above may, of course, also be used in other syntheses and is not limited to processes resulting in the formation of a β-substituted γ-amino carboxylic acid.

In a preferred embodiment of the present invention, $R^1$ is an alkyl group, preferably a linear or branched $C_1$- to $C_6$-alkyl group. More preferably, $R^1$ is iso-butyl. The latter may be used for the preparation of pregabalin.

In a preferred embodiment of the present invention, $R^2$ and $R^3$ are independently from one another selected from the group consisting of methyl, ethyl, propyl, iso-propyl, butyl, iso-butyl, sec-butyl, tert-butyl, phenyl, benzyl, methoxymethyl, benzyloxymethyl, $Li^+$, $K^+$, $Na^+$, $Cs^+$, and $NR_4^+$.

According to another preferred embodiment, $R^2$ and $R^3$ are forming a cyclopentyl or cyclohexyl ring together, or combined are $Mg^{2+}$.

The strong Brønsted acid S is preferably selected from the group consisting of HCl, HBr, $H_2SO_4$, and an alkyl or aryl sulfonic acid, such as MsOH (methanesulfonic acid), $CF_3SO_3H$, BsOH or pTsOH. Most preferred are MsOH or $H_2SO_4$. The preferred range for the amount of Brønsted acid S added is about 0.4 to 6.0 equivalents. However, the reaction does also work with higher amounts than 10 equivalents, if the water content is adjusted accordingly. Thus, larger amounts of the Brønsted acid S may be used as long as the water and/or solvent amount is increased also, but this economically and ecologically less preferred and may also lead to a decreased yield.

In a particularly preferred embodiment, 0.5 to 6.0 equivalents of MsOH or 0.4 to 2.5 equivalents of $H_2SO_4$ are used as the strong Brønsted acid S.

In a preferred embodiment, the one-pot conversion of (II) to (III) is conducted in the presence of 5 to 10 equivalents of water, more preferably 6 to 10 equivalents of water, with about 8 being optimal. By adding small amounts of water, the yield is further improved.

In a preferred embodiment, the one-pot conversion of (II) to (III) is carried out at a concentration of 0.3 to 1 M, more preferably at 0.4 to 0.6 M, most preferably at about 0.5 M. At this low concentration, the formation of by-products is significantly reduced.

Preferably, the one-pot conversion of (II) to (III) is carried out at a temperature of between 90° C. and 110° C. Temperatures above 120° C. may be feasible depending on the substrate, but may lead to stability problems and thus decreased yield.

The most preferred conditions involve about 2.5 equivalents of the strong Brønsted acid S, about 8 equivalents of water and a concentration of about 0.5 M.

In a preferred embodiment, the method of the present invention is applied to an enantiomerically enriched, more preferably to an enantiomerically pure starting material.

Throughout this application, a compound is "racemic" if it comprises the two enantiomers in a ratio of from 60:40 to 40:60, preferably in a ratio of about 50:50.

Throughout this application, a compound is "enantiomerically enriched" if it comprises more than 60% of one of the two enantiomers.

Throughout this application, a compound is "enantiomerically pure" if it comprises 95% or more of one of the two enantiomers, preferably 98% or more, more preferably 99% or more.

In a preferred embodiment, enantiomerically enriched, more preferably enantiomerically pure, (S)-pregabalin (S-IV*) is prepared. To this end, the substituted γ-nitro carboxylic acid (S-IX*) obtained by the hydrolysis/decarboxylation is further reduced to the corresponding γ-amino carboxylic acid.

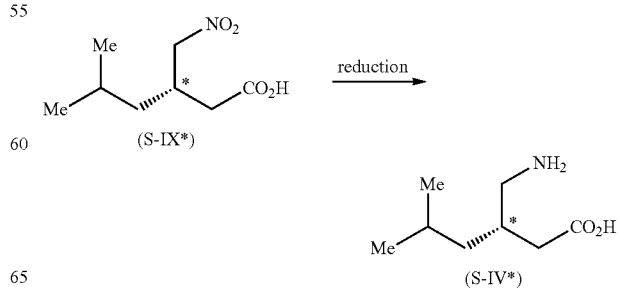

In order to arrive at an enantiomerically enriched—or even enantiomerically pure—final product (I*), several possible reaction sequences have been previously applied. For instance, it is possible to obtain an enantiomerically enriched β-substituted γ-nitro dicarboxylic acid ester (II*) by an asymmetric Michael addition reaction. Alternatively, it is also possible to prepare the β-substituted γ-amino carboxylic acid (I) in racemic form and subsequently resolve the racemate.

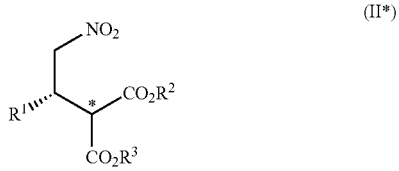

It has now been found that, as an alternative or in addition to the use of an enantiomerically enriched β-substituted γ-nitro dicarboxylic acid ester or dicarboxylate salt (II*), saponification of the β-substituted γ-nitro carboxylic acid (III)—or (III*), for that matter—provides a means for (further) increasing the enantiomeric excess of one enantiomer.

Therefore, in a further aspect, the present invention also relates to a method for the preparation of an enantiomerically enriched β-substituted γ-amino carboxylic acid of general formula (I*)

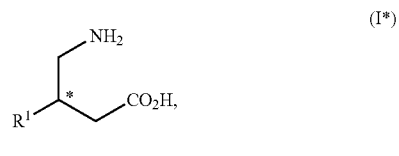

comprising a salt formation from a β-substituted γ-nitro carboxylic acid of general formula (III) to obtain the corresponding enantiomerically enriched β-substituted γ-nitro carboxylic acid salt of general formula (V*)

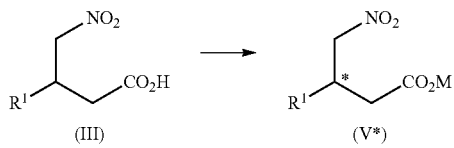

and subsequent crystallization or precipitation.

In this reaction, the β-substituted γ-nitro carboxylic acid of general formula (III) is racemic or enantiomerically enriched. If a racemic γ-nitro carboxylic acid is used, a chiral base must be applied in order to obtain an enantiomerically enriched salt. For an enantiomerically enriched γ-nitro carboxylic acid, on the other hand, the salt displays an improved enantiomeric ratio if prepared both with a chiral or with an achiral base.

In this reaction, $R^1$ is selected from the group consisting of $C_1$- to $C_{12}$-alkyl, alkenyl, alkynyl, and aryl. Preferably, $R^1$ is an alkyl group, preferably a linear or branched $C_1$- to $C_6$-alkyl group. More preferably, $R^1$ is iso-butyl.

M is an alkali metal cation, an alkaline earth metal cation or an organic amine. The organic amine may be a primary, secondary, tertiary or quarternary amine, and may further be chiral or achiral. Preferably, M is selected from the group consisting of $Li^+$, $K^+$, $Na^+$, $Cs^+$, $Mg^{2+}$ (in which case there are two nitro carboxylates per M), $NH_4^+$, $NR_4^+$, and $HNR_3^+$.

In general, the salt formation may be conducted using achiral amines, chiral amines or inorganic bases. Suitable reagents include, but are not limited to:

dicyclohexylamine, ethanolamine, diethanolamine, triethanolamine, ethylenediamine, diethylamine, n-propylamine, diisobutylamine, dibenzylamine, 3-phenyl-1-propylamine; (S)-3-methyl-2-amine, (S)-3,3-dimethyl-2-amine, (S)-1-cyclohexyl-ethylamine, cinchonine, quinidine; $Mg(OH)_2$, $Ca(OH)_2$, $KO^+Bu$, KOH, $K_2CO_3$, NaOMe, $NaOAc.3H_2O$, Na-2-ethylhexanoate, NaOH, $Na_2CO_3$. (see example 3). Most satisfying results were obtained using triethanolamine, dibenzylamine, NaOH, quinidine, (S)-1-cyclohexyl-ethylamine, diisopropylamine, and tert-butylamine.

Therefore, in a preferred embodiment, the salt formation is performed using a base selected from the group consisting of triethanolamine, dibenzylamine, NaOH, quinidine, (S)-1-cyclohexyl-ethylamine, diisopropylamine, and tert-butylamine.

Typically, about 1 equivalent of the base is used for the saponification. However, one main problem of this reaction is the instability of γ-nitro carboxylic acid salts, which easily undergo consecutive transformation to the corresponding N-hydroxy succinimide (XIV). Therefore, these salts should not be stored at elevated temperatures and should be used immediately for the hydrogenation step.

Surprisingly, it has now been found that treatment of the β-substituted γ-nitro carboxylic acid (III) with 2 or more equivalents of a strong base, such as KOH or NaOH, affords the corresponding nitronate salt (XXI).

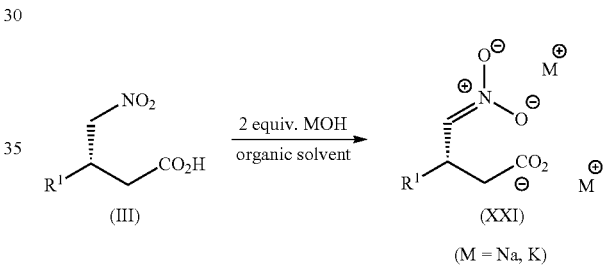

As shown in example 4, the enantiomeric excess was not improved by the disalt formation. However, the purity is significantly upgraded from 79% to >90%. In addition, these salts are very stable at room temperature.

Therefore, after upgrading the enantiomeric excess of the nitroacid (III) by the monosalt formation, the monosalts should be converted to the corresponding disalts for stability reasons and/or for an additional upgrade of the purity.

Therefore, in a preferred embodiment, the carboxylic acid salt (V*) is further converted to a nitronate salt of general formula (XXI*)

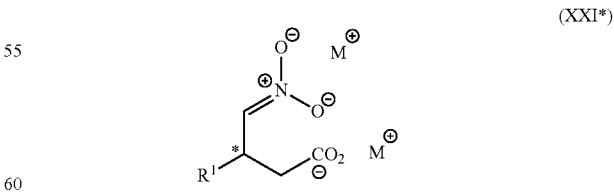

by treatment with a strong base selected from the group consisting of NaOH and KOH.

Preferably, a synthesis of a β-substituted γ-amino carboxylic acid of general formula (I) employs both the one-pot hydrolysis/decarboxylation and the salt formation of the present invention.

Therefore, in a preferred embodiment, the method of the present invention comprises both the one-pot conversion of a β-substituted γ-nitro dicarboxylic acid ester or of a β-substituted γ-nitro dicarboxylate of general formula (II) to a β-substituted γ-nitro carboxylic acid of general formula (III) and the salt formation from the β-substituted γ-nitro carboxylic acid of general formula (III) to the corresponding enantiomerically enriched β-substituted γ-nitro carboxylic acid salt of general formula (V*).

More preferably, the β-substituted γ-nitro carboxylic acid salt (V*) is further converted to the corresponding nitronate salt (XXI*).

The method of the present invention is particularly favorable for the preparation of (S)-pregabalin: Even though dialkyl 2-(4-methyl-1-nitropentan-2-yl) malonate may originally be prepared from 4-methyl-1-nitro-pent-ene by an asymmetric Michael addition, a purification step is necessary to obtain pregabalin in high quality. Since dialkyl 2-(4-methyl-1-nitropentan-2-yl) malonate is an oil, a purification by crystallization is not possible, necessitating a silica gel column chromatography, which is unfavorable for large scale. Also 5-methyl-3-(nitromethyl) hexanoic acid is an oil.

Thus, only the salt formation of the present invention, by which the corresponding nitro carboxylate salt is formed, allows for a purification by crystallization.

Alternatively, it is also possible to perform an enantiomeric separation or an upgrade in enantiopurity at a later stage of the synthesis. For instance, pregabalin may be subjected to recrystallization.

In a further aspect, the present invention also refers to an enantiomerically enriched β-substituted γ-nitro carboxylic acid salt of general formula (V*)

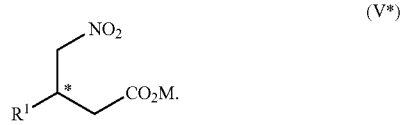

(V*)

In (V*), $R^1$ is selected from the group consisting of $C_1$- to $C_{12}$-alkyl, alkenyl, alkynyl, and aryl, and M is an alkali metal cation, an alkaline earth metal cation or an organic amine. The organic amine may be a primary, secondary, tertiary or quarternary amine, and may further be chiral or achiral.

Preferably, $R^1$ is an alkyl group, preferably a linear or branched $C_1$- to $C_6$-alkyl group. More preferably, $R^1$ is iso-butyl.

Preferably, M is selected from the group consisting of $Li^+$, $K^+$, $Na^+$, $Cs^+$, $Mg^{2+}$ (in which case there are two nitro carboxylates per M), $NH_4^+$, $NR_4^+$, and $HNR_3^+$.

In a further aspect, the present invention also refers to an enantiomerically enriched β-substituted γ-nitronate carboxylic acid salt of general formula (XXI*)

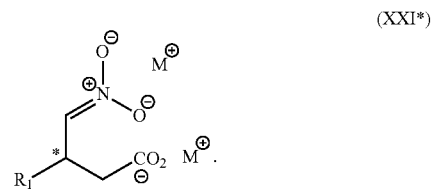

(XXI*)

In (XXI*), $R^1$ is selected from the group consisting of $C_1$- to $C_{12}$-alkyl, alkenyl, alkynyl, and aryl, and M is an alkali metal cation, an alkaline earth metal cation or an organic amine. The organic amine may be a primary, secondary, tertiary or quarternary amine, and may further be chiral or achiral.

Preferably, $R^1$ is an alkyl group, preferably a linear or branched $C_1$- to $C_6$-alkyl group. More preferably, $R^1$ is iso-butyl.

Preferably, M is selected from the group consisting of $Li^+$, $K^+$, $Na^+$, $Cs^+$, $Mg^{2+}$ (in which case there is only one M per nitronate carboxylate), $NH_4^+$, $NR_4^+$, and $HNR_3^+$.

In a preferred embodiment, the enantiomerically enriched β-substituted γ-nitro carboxylic acid salt (V*) and the enantiomerically enriched β-substituted γ-nitronate carboxylic acid salt (XXI*), respectively, are enantiomerically pure.

In a further aspect, the present invention refers to the use of the enantiomerically enriched β-substituted γ-nitro carboxylic acid salt (V*) and the enantiomerically enriched β-substituted γ-nitronate carboxylic acid salt (XXI*), respectively, for the preparation of an enantiomerically enriched β-substituted γ-amino carboxylic acid of general formula (I*).

Therefore, for all the methods and uses of the present invention described herein, as well as for the β-substituted γ-nitro carboxylic acid salts and the β-substituted γ-nitronate carboxylic acid salts of the present invention, the same substituents are preferred.

The present invention is further illustrated by the following examples, which are not to be considered as limiting:

EXAMPLE 1

Optimization of One-Pot Hydrolysis and Decarboxylation of Dimethyl 2-(4-methyl-1-nitropentan-2-yl) malonate (XVI)

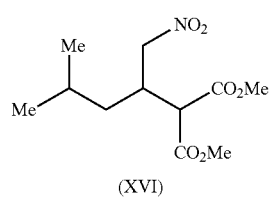

(XVI)

| $H^+$, $H_2O$
| AcOH
| 90-110° C.

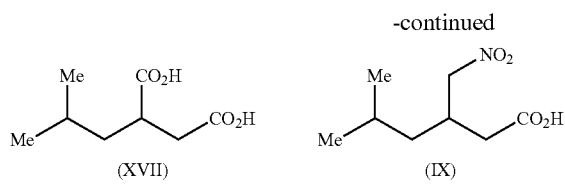
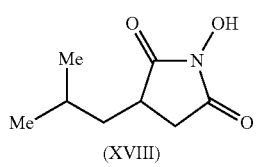

See tables 1a-1b below.

Due to previous non-satisfying results (entries 1-2), the one-pot hydrolysis/decarboxylation was investigated extensively. Optimization of the reaction started from HCl in water (entry 3) as described in WO 2009/147434. To reduce the formation of XVII, the amount of water was decreased by using AcOH as solvent instead, and also the amount of HCl was reduced (entry 4, 5). A slight increase of the amount of HCl from 6 to 8 did not improve the result. The amount of water was further decreased by using more concentrated HCl (entries 6 and 7), which improved the ratio of IX:XVII, but incomplete reaction was observed in entry 7 (HPLC: 44% of product with 10% of XVI).

Increasing the reaction temperature to 110° C. significantly accelerated the reaction, although the concentration and water amount were lowered (comparing entry 8 with entries 6-7). The reaction rate comes to limit and low conversion (HPLC: 5% of product) was observed when only 2.5 equiv. of HCl were used (entry 9).

To investigate the influence of acid amount without variation of the amount of water, MsOH was used as the strong acid S. Starting from 2.5 equiv., the ratio of IX:XVII was improved but about 10% of imide XVIII was also observed (entries 10 and 11). Although the reaction with 10 equiv. of water was carried out at 110° C., less than 10% of XVII was obtained. There was no by-product formation at 90° C. in the presence of various amounts of MsOH and water (entries 12, 13, and 14), however longer reaction time (1 d) was needed. Under these conditions (90° C., 8 equiv. of water, 0.5 M), XVII can be observed when using 4-6 equiv. of MsOH (comparing entry 14 with entries 18 and 19). Even though the reaction with a lower amount of MsOH (0.5-1.0 equiv.) was performed at a higher temperature (110° C.), still no XVII was formed (comparing entry 14 with entries 15 and 16). It comes to limit when the reaction is carried out with 2 equiv. of MsOH at 110° C. (comparing entry 15 with 17), where XVII was formed. Apparently, the amount of acid (0.5-2 equiv.) and temperature influence to the reaction rate: the higher the faster (entries 15-17 for acid amount and entries 11-12 for temperature). Using more than 3.5 equiv. of MsOH (entries 18-19) did not change the reaction rate significantly. The desired product can be obtained in >80% yield with 0.5-4 equiv. of MsOH (entries 15-18). The initial optimization shows that the formation of XVII and XVIII can be favorably suppressed.

In order to get a more robust procedure, Taguchi experiment (L9 array; see table 2) was performed (entries 20-28). Four factors (acid amount (A), concentration (C), water amount (W), and temperature (T)), each at 3 levels were considered.

TABLE 2

| Unit | MsOH (eq) | Water (eq) | T (° C.) | Conc. (M) |
| --- | --- | --- | --- | --- |
| 1 | 2.5 | 6 | 90 | 0.25 |
| 2 | 3.0 | 8 | 100 | 0.5 |
| 3 | 3.5 | 10 | 110 | 1.0 |

For most cases, the reaction gave high yield (>83%), except entry 24. For entries 25 and 28, low yield was obtained because of incomplete reaction (15% and 13%, respectively, as determined by $^1$H NMR). As shown in entries 20, 25, and 27, long reaction time is needed at 90° C. XVII is always formed if the reaction is conducted at high concentration (1.0 M; entries 22, 23, and 27) and is never observed at low concentration (0.5 M; entries 20, 24, and 28). The best yield was obtained in entry 21, where 2.5 equiv. of MsOH were used.

After performing statistical analysis of these results, the following significant process parameters were identified:

Factors influencing the reaction rate: T>C>W>A

Factors influencing the yield: A>W>C>T

Factors influencing the amount of XVII: C>A>W>T

Consequently, reaction with MsOH (2.5 equiv.), water (8 equiv.) at 0.5 M and 110° C. should provide the highest yield.

A confirmation experiment (entries 29 with racemic substrate and 30 with enantiomerically enriched substrate) was conducted to verify the optimal process parameters obtained from the process parameter design.

Scaling up economically by using crude Michael adduct under the same conditions (entries 31-32) gave product IX in about 70% yield over 2 steps (Michael addition and hydrolysis/dacarboxylation). Higher concentration showed again more by-product formation (entry 31).

To get more cost effective, MsOH was replaced by $H_2SO_4$ (entries 33-43). The by-products were exclusively formed if water amount was very low (1.2 equiv., entry 33). Using the best condition found for MsOH with $H_2SO_4$ (entry 34), 7% of XVII was formed. To evaluate the factors (A, W, and T), design of experiment was again performed (entries 36-39).

The best conditions (1.2 equiv. of $H_2SO_4$, 8 equiv. of water at 100 or 110° C., entries 40 and 41) were established by statistical analysis. This afforded the product IX in more than 80% yield over 2 steps (Michael addition and hydrolysis/dacarboxylation), which was higher than for MsOH (comparing entry 41 with entry 32). When using less $H_2SO_4$ (0.4 equiv.), the reaction time increased (entry 42), but almost the same result was obtained (comparing entry 41 with 42). Using recovered AcOH (~5.8% water contained), the reaction successfully took place to afford product IX in up to 94% HPLC yield (entry 43).

In conclusion, it was found that MsOH (0.5-6.0 equiv.) and $H_2SO_4$ (0.4-2.5 equiv.) can be used to perform the one-pot hydrolysis and decarboxylation reaction of XVI successfully. However, a significant amount of water (6-10 equiv.) is necessary to get gratifying results.

The reaction rate and the product ratio were mainly influenced by the reaction temperature (110° C.) and the concentration (0.5 M). When applying this robust procedure, exclusively the desired product IX was formed in up to 94% yield for one step (using pure XVI) or 70-87% yield over two steps (using crude XVI).

EXAMPLE 2

Optimization of One-Pot Hydrolysis and Decarboxylation of Dipotassium 2-(4-methyl-1-nitropentan-2-yl) malonate (XIX)

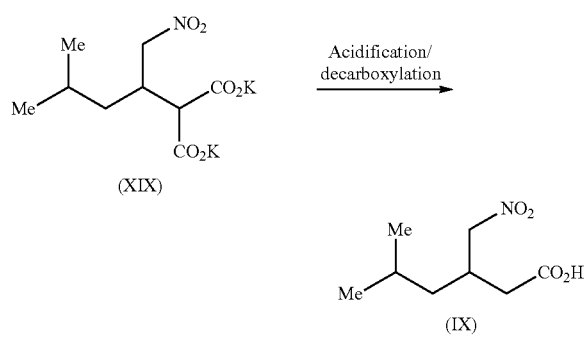

In the case of dicarboxylate XIX, when using 4-6 equiv. of MsOH, XVII was still observed in 4-11%. Using low amounts of MsOH (1-3 equiv.), 12-100% of by-products were obtained, mostly XVIII.

For enantiomerically enriched starting material, no erosion of enantiomeric ratio was observed.

EXAMPLE 3

Saponification of 5-Methyl-3-(nitromethyl) hexanoic Acid (IX) Using Various Bases

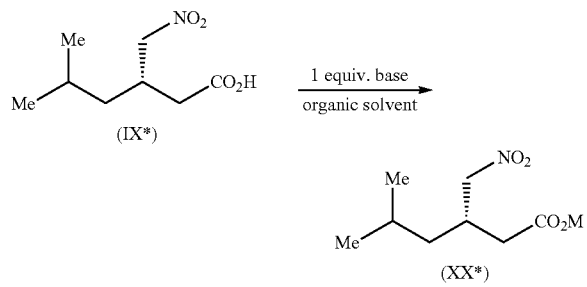

See tables 3a-3b below.

In all cases, crystallization or precipitation processes of XX* mono-salts using 1 equivalent of base have an essential influence on the separation of the enantiomers. The enantiomeric excess were upgraded from 86% ee to >90% ee. Especially, the best results were obtained by salt formation of (IX*) with NaOH (entry 6), diisopropylamine (entry 15), and (S)-1-cyclohexyl-ethylamine (entry 12).

Enantiomeric excess was improved up to 99% ee (entry 15). However, purities of some salts are lower than those of the starting material, and XVIII was observed by HPLC as a major side product. These results seem to indicate the stability problem of the mono-salts.

In contrast, purities of other salts were upgraded. However, those salts also decomposed to XVIII upon storage for a longer period. Therefore, these salts should be used immediately for hydrogenation.

EXAMPLE 4

Treatment of 5-Methyl-3-(nitromethyl) hexanoic Acid (IX) with 2 Equivalents of a Strong Base

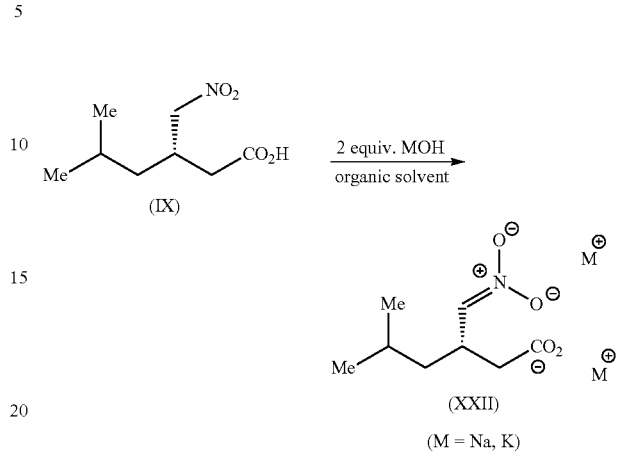

TABLE 4

| Base (equiv.) | ee of IX | HPLC purity of IX | solvent | t/T | ee of XXII | HPLC purity of XXII | Yield [%] |
|---|---|---|---|---|---|---|---|
| NaOH (2.5) | 85.9 | 86 | EtOH | 16 h at 20-25° C. | 83.7 | 90.7 | 79.0 |
| KOH (3.0) | 86.0 | 79.0 | EtOH/ MeCN 1:2 | 16 h at 20-25° C. | 83.8 | 97.2 | 96.2 |

(only precipitation conditions shown; the starting material was prepared by extraction and concentration of organic layer)

As shown in table 4, the enantiomeric excess was not improved by the disalt formation. However, the purity is significantly upgraded from 79% to >90%. In addition, these salts are very stable at room temperature.

EXAMPLE 5

Synthesis of 4-Methyl-1-nitro-pent-1-ene

An aqueous 10 M NaOH solution (9 ml, 90 mmol, 1 equiv.) was added dropwise to a solution of isovaleraldehyde (9.70 ml, 90 mmol, 1 equiv.) and nitromethane (4.90 ml, 90 mmol, 1 equiv.) in EtOH (150 ml) at 0° C. After 10 min, the reaction mixture was warmed to room temperature. After 4 h, a pale yellow foam was observed. Then, acetic acid (5.2 ml, 90 mmol, 1 equiv.) was slowly added, followed by addition of water (50 ml). The aqueous layer was extracted with MTBE (2×50 ml). The extracts were washed with water until the pH of the washings was 6. The organic layer was dried over $Na_2SO_4$, filtered, and concentrated in rotary evaporator affording a pale yellow crude oil of 3-methyl-1-(nitromethyl)-butanol (GC purity: 97.5%), which was used in the next step without further purification.

To a solution of 3-methyl-1-(nitromethyl)-butanol (1 equiv.) in $CH_2Cl_2$ (100 ml) at 0° C. was added MsCl (7 ml, 90 mmol, 1 equiv.). Triethylamine (25 ml, 180 mmol, 2 equiv.) was then added dropwise. The reaction mixture was stirred for 30 min at 0° C., followed by pouring to a cold 10% HCl solution (30 ml) in separatory funnel. The organic layer was separated and washed with brine (50 ml), dried over $Na_2SO_4$, filtered, and concentrated in rotary evaporator.

The residue was passed through a short Silica gel plug (eluent: 5% Et$_2$O in cyclohexane) to afford 4-methyl-1-nitro-pent-1-ene as a yellow oil in 78-81% yield over 2 steps (GC purity: 98.5%).

EXAMPLE 6

Synthesis of 4-[(R)-(5-ethenyl-1-azabicyclo [2.2.2] octan-2-yl)-hydroxymethyl]quinolin-6-ol (Cupreidine)

Under N$_2$-atmosphere, dodecanethiol (9.6 ml, 40 mmol, 2.0 equiv.) was dissolved in DMF (40 ml). KO$^t$Bu (4.5 g, 40 mmol, 2.0 equiv.) was added (exothermic). The obtained white suspension was stirred for 5-10 min. Quinidine (6.49 g, 20 mmol, 1.0 equiv.) was added in one portion. The obtained yellow suspension was heated to 110° C. for 7 h and was monitored by HPLC. After cooling to room temperature, the reaction was quenched with saturated NH$_4$Cl (100 ml, pH=8-9). The orange solution was extracted with CH$_2$Cl$_2$ (2×70 ml). The combined organic layers were extracted with 1N HCl (100 ml). The aqueous layer was washed with cyclohexane (40 ml) to remove dodecanethiol and methyl dodecanethiolate. The pH of aqueous layer was adjusted to 7.5-8 with 30% NaOH solution and then extracted with CH$_2$Cl$_2$ (2×100 ml). The combined organic layers were dried over Na$_2$SO$_4$, filtered, and completely concentrated in rotary evaporator to obtain an orange oil of crude product. This crude product was dissolved in CH$_2$Cl$_2$ (100 ml) and washed with brine (2×50 ml). The organic layer was dried over Na$_2$SO$_4$), filtered and completely concentrated in rotary evaporator to obtain an orange residue. The residue was then dissolved in 1N NaOH (80 ml). Sodium chloride (15 g) and water (20 ml) were added. After stirring for 30 min, 2N HCl (35 ml) was added and the pH was adjusted to 9.0-9.5. The beige suspension was stirred at room temperature for 3 h and was then filtered. The filtercake was washed with water (3×10 ml). After drying at 60° C. for 18 h in vacuum, a beige powder of cupreidine was obtain in 85% yield (HPLC-purity: 85.9% along with dihydrocupreidine in 11.8%).

EXAMPLE 7

Synthesis of (S)-(3-Methyl-1-nitromethyl-butyl)-malonic acid dimethyl Ester (VI)

At −15° C., to a solution of 4-methyl-1-nitro-pent-1-ene (13 g, 100 mmol, 1 equiv.) in MTBE (50 ml, 2M) was added catalyst cupreidine (2.8 g, 9 mol %), and dimethyl malonate (13 ml, 103 mmol, 1.03 equiv.). The resulting mixture was stirred at −10° C. and was monitored by GC. After 40 h, 2M HCl (40 ml) was added. Product was extracted with toluene (2×40 ml). The combined organic layers were washed with water (40 ml) and concentrated in rotary evaporator to give crude VI as yellow oil (86% ee, HPLC-purity: 97.3%)

The aqueous phase containing upreidine was adjusted to a pH of 8.5-9.0 with NaOH palettes and 32% HCl. Catalyst was filtered and dried. The pale yellow powder was obtained in 91% yield (HPLC-purity: 85.1% along with dihydrocupreidine 12.5%).

EXAMPLE 8

Synthesis of Dipotassium-(3-methyl-1-nitro-methyl-butyl)-malonate (XIX)

A solution of KOH (1.60 g, 28 mmol, 3.5 equiv.) in water (2 ml) and MeOH (32 ml) was introduced successively into a solution of VI (2.04 g, 8 mmol, 1 equiv.) in MeOH (4 ml). The mixture was stirred at room temperature for 16 h. The reaction was concentrated in rotary evaporator to give a yellow sticky solid. To this solid, acetone (15 ml) and MeOH (4 ml) was slowly added. A pale yellow solid was obtained and was filtered to get XIX in 95% yield (HPLC-purity: 88.0%).

EXAMPLE 9

Synthesis of (S)-5-methyl-3-nitromethyl-hexanoic Acid ((S)-IX)

MsOH:

To a solution of XVI (86.5% ee, 13.10 g, 50 mmol, 1 equiv.) in AcOH (100 ml) was added MsOH (8.20 ml, 125 mmol, 2.5 equiv.) and water (7.20 ml, 400 mmol, 8 equiv.). This mixture was heated to 110° C. and was monitored by HPLC. After 8 h, the reaction mixture was diluted with water (50 ml) and saturated NaCl (50 ml). Product was extracted with toluene (2×80 ml). The combined organic layers were concentrated in rotary evaporator. The residue was purified by flash column chromatography (5-10% EtOAc in CH$_2$Cl$_2$ with 0.1% AcOH) to give (S)-IX as yellow oil in 88% yield based on VI (HPLC-purity: 90.9%). To determine ee, esterification with 3M HCl in MeOH was carried out leading to ethyl 5-methyl-3-(nitromethyl)hexanoate in quantitative yield with 86.6% ee.

Using the same procedure with crude XVI: IX* was obtained in 68% isolated yield based on 4-methyl-1-nitro-pent-1-ene with 86% ee (HPLC-purity: 93.0%).

H$_2$SO$_4$:

To a solution of crude XVI (86% ee, 15 mmol, 1 equiv.) in AcOH (30 ml, 0.5 M) was added 97% H$_2$SO$_4$ (1.0 ml, 18 mmol, 1.2 equiv.) and water (2.2 ml, 120 mmol, 8 equiv.). This mixture was heated to 110° C. and was monitored by HPLC (HPLC yield: 87.8%). After 9 h, the reaction mixture was concentrated in rotary evaporator (19% left by weight). Water was added to the obtained brown oil (13 ml) and the mixture was extracted with toluene (2×13 ml). The combined organic layers were concentrated in rotary evaporator to give crude (S)-IX as a brown oil (HPLC-purity: 86.7%). Some product was converted to ethyl 5-methyl-3-(nitromethyl)hexanoate with 3M HCl in MeOH to give quantitative yield with 86% ee.

Starting from dipotassium-(3-methyl-1-nitromethyl-butyl)-malonate (XIX):

To a solution of XIX (206 mg, 0.67 mmol, 1 equiv.) in AcOH (0.5 ml) was added MsOH (0.2 ml, 3.02 mmol, 4.5 equiv.) and water (0.1 ml, 5.36 mmol, 8 equiv.). This mixture was heated to 110° C. and was monitored by HPLC. After 3 h, the reaction was complete. Saturated NaCl solution (1 ml) and water (1 ml) were added. Product was extracted with toluene (3×1 ml). Solvents were evaporated to give a yellow crude oil with a 89:11 mixture of (S)-IX and XVII (HPLC-purity: 71.8%).

EXAMPLE 10

Synthesis of Pregabalin

To a solution of (S)-IX (89% ee, 8.45 g, 44.7 mmol, 1 equiv.) in MeOH (45 ml) was added palladium on charcoal in water (5.43 g, 1.12 mmol, 2.5 mol %). The mixture was hydrogenated with Parr apparatus at 3.5-4 atm of hydrogen gas for 16 h at room temperature. Upon completion, the reaction mixture was filtered through a Celite plug and washed with MeOH (50 ml) and water (150-200 ml). The solvent was removed by rotary evaporator to afford pregabalin as white solid in 85% yield (HPLC-purity: 80.3%).

EXAMPLE 11

Synthesis of Nitro Acid Dibenzylammonium Salt (XXIII)

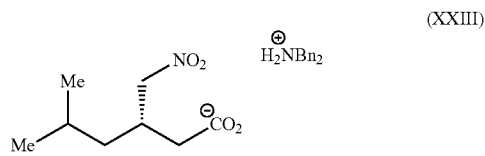

(XXIII)

Dibenzylamine (96 µl, 0.5 mmol) was added to a solution of nitro acid (S)-IX (95 mg, 0.5 mmol; ee: 85.4%, HPLC purity 91%) in THF (1 ml) was stirred. The clear solution was concentrated. The residue was cooled to 0° C. for 16 hours. THF (200 µl) and $^i$Pr$_2$O (150 µl) were added to the residue and gave a suspension. The suspension was heated, then the mixture was cooled to room temperature and re-precipitated. After centrifugation of the suspension, mother liquor was removed and the solid was dried under vacuum at room temperature to give nitro acid dibenzylammonium salt XIX as a colorless solid (yield: 70 mg, 0.18 mmol; ee: 90.2%; HPLC purity: 62.4%).

EXAMPLE 12

Synthesis of Nitro Acid Sodium Salt (XXIV)

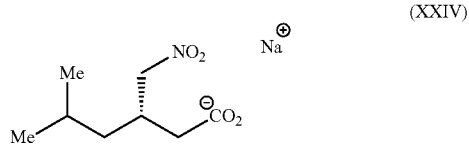

(XXIV)

NaOH (20 mg, 0.5 mmol) was added to a solution of nitro acid (S)-IX (95 mg, 0.5 mmol; ee: 86.6%, HPLC purity: 90.9%) in MeOH (1 ml) and was stirred. The mixture was evaporated to dryness and $^i$PrOH (1 ml) was added, stirred for 16 hours, and gave a suspension. The solid was separated by centrifugation of the suspension and washed with $^i$PrOH (0.5 ml). After centrifugation of the suspension, the solid was separated and dried under vacuum at room temperature to give nitro acid sodium salt XXVI as a colorless solid (yield: 48 mg, 0.23 mmol; ee: 95.3%; HPLC purity: 96.7%).

EXAMPLE 13

Synthesis of Nitro Acid Quinidinium Salt (XXV)

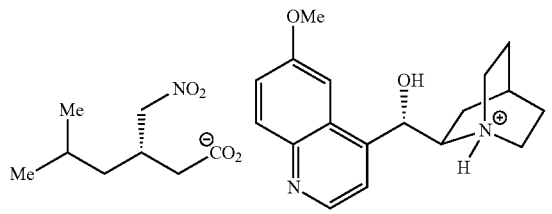

(XXV)

Quinidine (162 mg, 0.5 mmol) was added to a solution of nitro acid (S)-IX (95 mg, 0.5 mmol; ee: 85.4%, HPLC purity 91%) in MTBE (1 ml) and was stirred for 16 hours to afford a suspension. The solid was separated by centrifugation of the suspension and MTBE (0.5 ml) was added to the solid. The suspension was centrifuged again, the solid was separated and dried under vacuum at room temperature to give nitro acid quinidinium salt XXV as a colorless solid (yield: 185 mg, 0.38 mmol; ee: 91.2%; HPLC purity: 85.3%).

EXAMPLE 14

Synthesis of Nitro Acid (S)-1-cyclohexyl-ethylammonium Salt (XXVI)

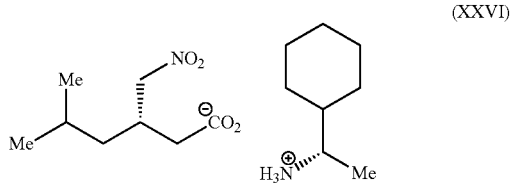

(XXVI)

(S)-1-Cyclohexyl-ethylamine (0.35 ml, 2.33 mmol) was added to a solution of nitro acid (S)-IX (475 mg, 2.33 mmol; ee: 86.0%, HPLC purity 92.0%) in MTBE (5 ml) and was stirred for 0.75 hours to afford a thick suspension. The suspension was diluted with MTBE (2.5 ml). After filtration of suspension, the solid was dried under vacuum at room temperature to give nitro acid (S)-1-cyclohexyl-ethylammonium salt XXVI as a colorless solid (yield: 615 mg, 1.95 mmol; ee: 95.0%; HPLC purity: 99.6%).

EXAMPLE 15

Synthesis of Nitro Acid Diisopropylammonium Salt (XXVII)

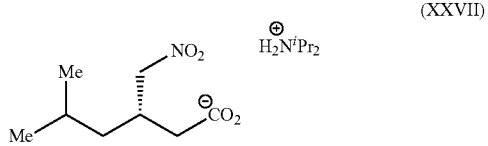

(XXVII)

Diisopropylamine (70 µl, 0.5 mmol) was added to a solution of nitro acid (S)-IX (95 mg, 0.5 mmol, ee: 86.6%, HPLC purity: 90.9%) in MTBE (1 ml) and was stirred for 20 hours to afford a thick suspension. The suspension was diluted with MTBE (2.5 ml). After filtration of the suspension, the solid was dried under vacuum at room temperature to give nitro acid diisopropylammonium salt XXVII as a colorless solid (yield: 44 mg, 0.15 mmol; ee: 99.4%; HPLC purity: 82.3%).

EXAMPLE 16

Synthesis of Nitro Acid Tert-Butylammonium Salt (XXVIII)

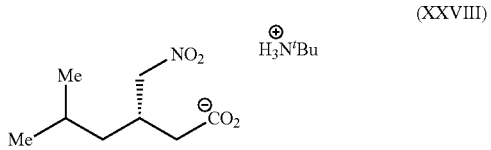

tert-Butylamine (52 μl, 0.5 mmol) was added to a solution of nitro acid (S)-IX (95 mg, 0.5 mmol, ee: 85.4%, HPLC purity 91%) in EtOAc (1 ml) and was stirred for 21 hours to afford a suspension. The solid was separated by centrifugation of the suspension and EtOAc (0.5 ml) was added to the solid. The suspension was centrifuged again, the solid was separated and dried under vacuum at room temperature to give nitro acid tert-butylammonium salt XXVIII as colorless solid (yield: 44.5 mg, 0.17 mmol; ee: 95.5%; HPLC purity: 78.1%).

EXAMPLE 17

Synthesis of Nitronate Di-Sodium Salt (XXIX)

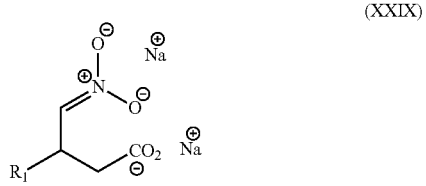

NaOH (396 mg, 4.95 mmol) was added to a solution of nitro acid (S)-IX (635 mg, 3.35 mmol, ee: 85.9%, HPLC purity: 86.0%) in EtOH (10 ml) and was stirred for 16 hours to afford a suspension. The solid was filtrated and washed with EtOH (4 ml) and then dried under vacuum at room temperature to give nitronate di-sodium salt XXIX as a pale yellow solid (yield: 617 mg, 2.26 mmol; ee: 83.7%; HPLC purity: 90.7%).

EXAMPLE 18

Synthesis of Nitronate Di-Potassium Salt (XXX)

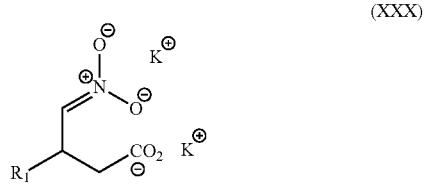

A solution of nitro acid (S)-IX (496 mg, 2.62 mmol) in MeCN (10 ml) was added to a solution of potassium hydroxide (441 g, 7.87 mmol, ee: 86.0%, HPLC purity: 79%) in EtOH (0.5 ml) and was stirred for 16 hours to afford a suspension. The solid was filtrated and washed with absolute MeCN (0.3 ml) and then dried under vacuum at room temperature to give nitronate di-potassium salt XXX as a pale yellow solid (yield: 667 mg, 2.52 mmol; ee: 83.8%; HPLC purity: 97.2%).

TABLE 1a

| # | XVI (mmol) | H+ (eq) | AcOH (M) | water (eq) | T (° C.) | time (h) | IX:XVII:XVIII[a] | % HPLC yield[b] |
|---|---|---|---|---|---|---|---|---|
| 1 | 0.76 | 48% HBr (8.7) | — | 42 | 115 | 16 | 0:100:0 | — |
| 2 | 0.76 | 30% HCl (8.7) | — | 34 | 105 | 14 | 46:54:0 | 38 |
| 3 | 1 | 32% HCl (71) | — | 530 | 100 | 8 | 33:67:0 | — |
| 4 | 0.50 | 32% HCl (6) | 1.0 | 26 | 100 | 12 | 74:26:0 | — |
| 5 | 0.50 | 1M HCl/AcOH (2), 32% HCl (6) | 0.5 | 26 | 100 | 12 | 65:35:0 | — |
| 6 | 0.50 | 1M HCl/AcOH (2), 37% HCl (6) | 0.5 | 21 | 100 | 11 | 77:23:0 | — |
| 7 | 0.50 | 37% HCl (6) | 1.0 | 21 | 100 | 11 | 80:20:0 | 90% conv. |
| 8 | 1.0 | 37% HCl (5) | 0.5 | 8 | 110 | 6 | 82:18:0 | 46.5 |
| 9 | 1.0 | 37% HCl (2.5) | 0.5 | 8 | 110 | 10 | nd | 48% conv. |
| 12 | 0.25 | MsOH (2.5) | 0.5 | 10 | 110 | 15 | 93:7:0 | — |
| 13 | 0.25 | MsOH (3.0) | 0.5 | 10 | 110 | 10 | 94:6:0 | — |
| 14 | 0.25 | MsOH (3.0) | 0.5 | 10 | 90 | 24 | 100:0:0 | — |
| 15 | 0.25 | MsOH (3.0) | 0.5 | 6 | 90 | 24 | 100:0:0 | — |
| 16 | 0.25 | MsOH (3.5) | 0.5 | 8 | 90 | 24 | 100:0:0 | — |
| 17 | 1.0 | MsOH (0.5) | 0.5 | 8 | 110 | 16 | 100:0:0 | 81.8 |
| 18 | 1.0 | MsOH (1.0) | 0.5 | 8 | 110 | 10 | 100:0:0 | 80.8 |
| 19 | 1.0 | MsOH (2.0) | 0.5 | 8 | 110 | 8 | 92:8:0 | 84.6 |
| 20 | 0.25 | MsOH (4.0) | 0.5 | 8 | 90 | 18 | 92:8:0 | 83.1 |
| 21 | 0.25 | MsOH (6.0) | 0.5 | 8 | 90 | 18 | 90:10:0 | — |
| 22 | 0.25 | MsOH (2.5) | 0.25 | 6 | 90 | 20 | 100:0:0 | 84.3 |
| 23 | 0.25 | MsOH (2.5) | 0.5 | 8 | 100 | 10 | 100:0:0 | 92.6 |
| 24 | 0.25 | MsOH (2.5) | 1.0 | 10 | 110 | 5 | 90:10:0 | 84.9 |
| 25 | 0.25 | MsOH (3.0) | 1.0 | 6 | 100 | 10 | 88:12:0 | 83.5 |

[a]determined by 1H NMR spectrum;
[b]determined by quantitative HPLC

TABLE 1b

| # | XVI (mmol) | H+ (eq) | AcOH (M) | water (eq) | T (° C.) | time (h) | IX:XVII:XVIII[a] | % HPLC yield[b] |
|---|---|---|---|---|---|---|---|---|
| 26 | 0.25 | MsOH (3.0) | 0.25 | 8 | 110 | 10 | 100:0:0 | 79.6 |
| 27 | 0.25 | MsOH (3.0) | 0.5 | 10 | 90 | 14 | 100:0:0 | 75.3 |
| 28 | 0.25 | MsOH (3.5) | 0.5 | 6 | 110 | 7.5 | 96:4:0 | 88.5 |
| 29 | 0.25 | MsOH (3.5) | 1.0 | 8 | 90 | 17 | 87:13:0 | 85.9 |
| 30 | 0.25 | MsOH (3.5) | 0.25 | 10 | 100 | 10 | 100:0:0 | 72.4 |
| 31 | 5 | MsOH (2.5) | 0.5 | 8 | 110 | 6 | 100:0:0 | 94.8 |
| 32 | 5[c] | MsOH (2.5) | 0.5 | 8 | 110 | 8 | 100:0:0 | 94.1 |
| 33 | 33[c] | MsOH (2.5) | 0.67 | 8 | 110 | 7 | 94:6:0 | 70.5 (2 steps) |
| 34 | 50[c] | MsOH (2.5) | 0.5 | 8 | 110 | 8 | 100:0:0 | 68.3 (2 steps) |
| 35 | 0.25 | 97% H$_2$SO$_4$ (8) | 0.5 | 1.2 | 100 | 10 | 0:80:20 | — |
| 36 | 0.5 | 97% H$_2$SO$_4$ (2.5) | 0.5 | 8 | 110 | 6 | 93:7:0 | 75.9 |
| 37 | 0.5 | 97% H$_2$SO$_4$ (1.5) | 0.5 | 8 | 110 | 6 | 94:6:0 | 76.2 |
| 38 | 1.0 | 97% H$_2$SO$_4$ (1.2) | 0.5 | 8 | 100 | 15 | 93:7:0 | 84.0 |
| 39 | 1.0 | 97% H$_2$SO$_4$ (1.2) | 0.5 | 8 | 110 | 7 | 96:4:0 | 87.6 |
| 40 | 1.0 | 97% H$_2$SO$_4$ (1.5) | 0.5 | 8 | 110 | 7 | 91:9:0 | 84.2 |
| 41 | 1.0 | 97% H$_2$SO$_4$ (1.5) | 0.5 | 8 | 100 | 15 | 91:9:0 | 82.9 |
| 42 | 15[c] | 97% H$_2$SO$_4$ (1.2) | 0.5 | 8 | 100 | 18 (3 h at 110) | 95:5:0 | 80.5 (2 steps) |
| 43 | 15[c] | 97% H$_2$SO$_4$ (1.2) | 0.5 | 8 | 110 | 9 | 95:5:0 | 87.8 (2 steps) |
| 44 | 4[c] | 97% H$_2$SO$_4$ (0.4) | 0.5 | 8 | 110 | 16 | 95:5:0 | 85.1 (2 steps) |
| 45 | 3.9[c] | 97% H$_2$SO$_4$ (1.2) | 0.5 | 8 | 110 | 10 | 97:3:0 | 94.1 |

[a]determined by 1H NMR spectrum;
[b]determined by quantitative HPLC;
[c]using enantiomerically enriched (S)-XVI TABLE 3a

| # | ee of IX | HPLC purity of IX | base (equiv.) | solvent | t/T | ee of XX | HPLC purity of XX | Yield [%] |
|---|---|---|---|---|---|---|---|---|
| 1 | 85.4 | 91 | Triethanolamine (1.0) | EtOH | 16 h at 0° C. | 91.2 | 45.7 | — |
| 2 | 85.4 | 91 | Triethanolamine (1.0) | EtOAc | 16 h at 0° C. | 91.7 | 63.1 | — |
| 3 | 85.4 | 91 | Dibenzylamine (1.0) | EtOH | Heat gun → 20-25° C. | 87.1 | 63.5 | 34 |
| 4 | 85.4 | 91 | Dibenzylamine (1.0) | THF/$^i$PrOH 4:3 | Heat gun → 20-25° C. | 90.2 | 62.4 | 36 |
| 5 | 86.6 | 90.9 | NaOH (1.0) | NeOH → $^i$PrOH[d] | 16 h at 20-25° C. | 95.1 | 96.7 | 45.6 |
| 6 | 86.6 | 90.9 | NaOH (1.0) | NeOH → MeCN[d] | 16 h at 20-25° C. | 96.5 | 87.6 | 72.7 |
| 7 | 86.6 | 90.9 | NaOH (1.0) | NeOH → MTBE[d] | 16 h at 20-25° C. | 92.4 | 62.3 | 85.1 |
| 8 | 86.6 | 90.9 | NaOH (1.0) | NeOH → acetone[d] | 16 h at 20-25° C. | 95.3 | 96.7 | 24.1 |
| 9 | 85.4 | 91 | Quinidine (1.0) | MTBE | 16 h at 20-25° C. | 91.2 | 85.3 | 76.2 |

[d]The mono-sodium salt was prepared in MeOH, the sample was evaporated and organic solvents were added to residue TABLE 3b

| # | ee of IX | HPLC purity of IX | base (equiv.) | solvent | t/T | ee of XX | HPLC purity of XX | Yield [%] |
|---|---|---|---|---|---|---|---|---|
| 10 | 86.6 | 90.9 | (S)-1-cyclohexyl-ethylamine (1.0) | MeCN | 20 h at 20-25° C. | 93.1 | 96.1 | 70.0 |
| 11 | 86.0 | 92.0 | (S)-1-cyclohexyl-ethylamine (1.0) | MTBE | 0.75 h at 20-25° C. | 95.0 | 99.6 | 83.7 |
| 12 | 86.6 | 90.9 | (S)-1-cyclohexyl-ethylamine (1.0) | PhMe | 20 h at 20-25° C. | 97.3 | 94.6 | 27.0 |
| 13 | 86.6 | 90.9 | (S)-1-cyclohexyl-ethylamine (1.0) | EtOAc | 20 h at 20-25° C. | 96.0 | 96.6 | 58.0 |
| 14 | 86.6 | 90.9 | diisopropylamine (1.0) | EtOAc | 20 h at 20-25° C. | 98.6 | 90.9 | 19.0 |
| 15 | 86.6 | 90.9 | diisopropylamine (1.0) | MTBE | 20 h at 20-25° C. | 99.4 | 82.3 | 30.5 |
| 16 | 86.6 | 90.9 | diisopropylamine (1.0) | THF | 20 h at 20-25° C. | 95.9 | 74.6 | 53.0 |
| 17 | 85.4 | 91 | tert-butylamine (1.0)[e] | EtOAc | 21 h at 20-25° C. | 95.5 | 78.1 | 34.0 |
| 18 | 85.4 | 91 | tert-butylamine (1.0)[e] | PhMe | 21 h at 20-25° C. | — | 65.5 | 11.0 |

[e]Only precipitation conditions indicated

The invention claimed is:

1. Method for the preparation of a (β-substituted γ-amino carboxylic acid of general formula (I)

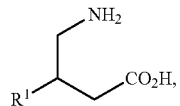
(I)

comprising a one-pot conversion of a β-substituted γ-nitro dicarboxylate of general formula (II) to a β-substituted γ-nitro carboxylic acid of general formula (III)

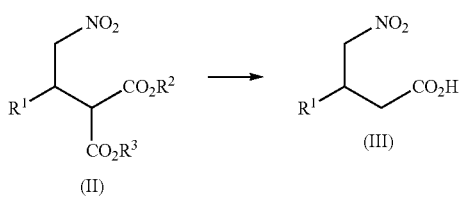

and a subsequent reduction of the γ-nitro group to an amine group,
wherein
$R^1$ is selected from the group consisting of $C_1$- to $C_{12}$-alkyl, alkenyl, alkynyl, and aryl, and
$R^2$ and $R^3$ are independently from one another selected from the group consisting of a $C_1$- to $C_{12}$-alkyl or aryl group, an alkali metal ion or a tetra-substituted ammonium ion, or $R^2$ and $R^3$ are together forming a $C_3$- to $C_{12}$-alkyl, alkenyl or aryl ring structure or are an alkaline earth metal ion,
wherein
the one-pot conversion of (II) to (III) involves the treatment of (II) with 0.2 to 10 equivalents of a strong Brønsted acid using a carboxylic acid as solvent, in the presence of 1 to 15 equivalents of water, at a temperature of between 90° C. and 120° C. and a concentration of less than 1 M, and
wherein the strong Brønsted acid is MsOH (methanesulfonic acid) or $H_2SO_4$.

2. Method according to claim 1, wherein $R^1$ is an alkyl group.

3. Method according to claim 1, wherein 0.5 to 6.0 equivalents of MsOH or 0.4 to 2.5 equivalents of $H_2SO_4$ are used as the strong Brønsted acid S.

4. Method according to claim 1, wherein the one-pot conversion of (II) to (III) is conducted in the presence of 5 to 10 equivalents of water.

5. Method according to claim 1, wherein the one-pot conversion of (II) to (III) is carried out at a concentration of 0.4 to 0.6 M.

6. Method according to claim 1, wherein enantiomerically enriched (S)-pregabalin (S-IV*)

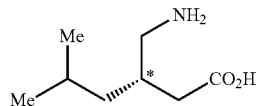
(S-IV*)

is prepared.

7. Method according to claim 1, wherein the strong Brønsted acid is MsOH.

8. Method according to claim 1, wherein the strong Brønsted acid is $H_2SO_4$.

9. Method for the preparation of a β-substituted γ-amino carboxylic acid of general formula (I)

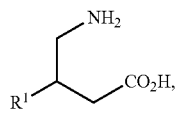
(I)

comprising a one-pot conversion of a β-substituted γ-nitro dicarboxylate late of general formula (II) to a β-substituted γ-nitro carboxylic acid of general formula (III)

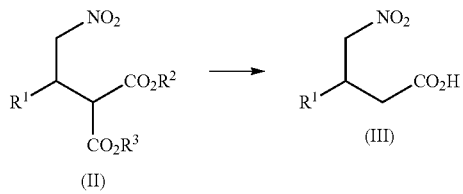

and a subsequent reduction of the γ-nitro group to an amine group,
wherein
$R^1$ is selected from the group consisting of $C_1$- to $C_{12}$-alkyl, alkenyl, and aryl, and
$R^2$ and $R^3$ are independently from one another selected from the group consisting of a $C_1$- to $C_{12}$-alkyl or aryl group, an alkali metal ion or a tetra-substituted ammonium ion, or $R^2$ and $R^3$ are together forming a $C_3$- to $C_{12}$-alkyl, alkenyl or aryl ring structure or are an alkaline earth metal ion,
wherein
the one-pot conversion of (II) to (III) involves the treatment of with 0.2 to 10 equivalents of a strong Brønsted acid using a carboxylic acid as solvent, in the presence of 1 to 15 equivalents of water, at a temperature of between 90° C. and 120° C. and a concentration of less than 1 M, wherein an enantiomerically enriched (β-substituted γ-amino carboxylic acid of general formula (I*)

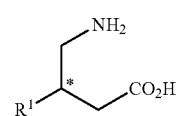
(I*)

is prepared,
the method further comprising a salt formation from a β-substituted γ-nitro carboxylic acid of general formula (III) to obtain the corresponding enantiomerically enriched β-substituted γ-nitro carboxylic acid salt of general formula (V*)

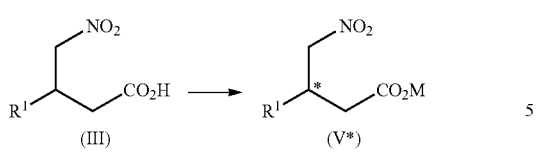

and subsequent crystallization or precipitation, wherein
the β-substituted γ-nitro carboxylic acid of general formula (III) is racemic or enantiomerically enriched, and
M is an alkali metal cation, an alkaline earth metal cation or an organic amine.

10. Method according to claim 9, wherein the salt formation is performed using a base selected from the group consisting of triethanolamine, dibenzylamine, NaOH, quinidine, (S)-1-cyclohexyl-ethylamine, diisopropylamine, and tert-butylamine.

11. Method according to claim 9, wherein the carboxylic acid salt (V*) is further converted to a nitronate salt of general formula (XXI*)

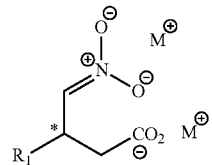

by treatment with a strong base selected from the group consisting of NaOH and KOH.

* * * * *